United States Patent [19]

Wideman

[11] 4,131,627
[45] Dec. 26, 1978

[54] CONTINUOUS HYDROGENATION OF CYCLOPENTADIENE TO CYCLOPENTENE USING A RANEY NICKEL CATALYST SATURATED WITH AMMONIA

[75] Inventor: Lawson G. Wideman, Akron, Ohio

[73] Assignee: The Goodyear Tire & Rubber Company, Akron, Ohio

[21] Appl. No.: 850,578

[22] Filed: Nov. 11, 1977

[51] Int. Cl.$^2$ ............................................. C07C 5/02
[52] U.S. Cl. .............................. 260/666 A; 260/667; 260/683.9
[58] Field of Search ................................... 260/666 A

[56] References Cited

U.S. PATENT DOCUMENTS 3,637,877   1/1972   Nowack et al. ................. 260/666 A Primary Examiner—Veronica O'Keefe
Attorney, Agent, or Firm—J. Y. Clowney

[57] ABSTRACT

There is disclosed a process for the preparation of cyclopentene from cyclopentadiene which comprises selectively hydrogenating cyclopentadiene in the liquid phase by continuously contacting cyclopentadiene with hydrogen while passing the mixture of hydrogen and cyclopentadiene through a highly dispersed form of nickel catalyst which nickel has been treated with ammonia.

2 Claims, No Drawings

CONTINUOUS HYDROGENATION OF CYCLOPENTADIENE TO CYCLOPENTENE USING A RANEY NICKEL CATALYST SATURATED WITH AMMONIA

BACKGROUND OF THE INVENTION

This invention is directed to selective hydrogenation of dienes to monoolefins, particularly of cyclopentadiene to cyclopentene. More specifically, it is directed to a process where cyclopentadiene is selectively hydrogenated to cyclopentene in which a mixture of cyclopentadiene and hydrogen are passed through a catalyst comprising a highly dispersed nickel which has been saturated with ammonia.

At the present time substantial amounts of cyclopentadiene usually in the form of dicyclopentadiene are available as a byproduct from the process of steam cracking of naphtha in order to produce ethylene. Cyclopentene has been found to be useful as a monomer for the formation of general purpose elastomers by ring opening polymerization. Therefore, it is desirable to convert a portion of the excess cyclopentadiene available into a more valuable raw material, cyclopentene.

The hydrogenation of cyclopentadiene to cyclopentene is not new. In U.S. Pat. No. 3,751,499, cyclopentadiene has been continuously converted to cyclopentene using a palladium on alumina catalyst. In U.S. Pat. Nos. 3,472,763, 3,915,891 and 3,819,734 further describe the conversion of cyclopentadiene into cyclopentene by the use of nickel salts as the catalyst. Other U.S. patents which relate to the non-continuous preparation of cyclopentene from cyclopentadiene are 3,857,894; 3,994,986; and 2,360,555.

However, none of these patents disclose the invention hereinafter described.

The cyclopentadiene employed to form cyclopentene by the use of the present invention is usually obtained by depolymerizing or cracking of dicyclopentadiene. The depolymerization of dicyclopentadiene is usually accomplished by heating the dimer at a temperature above 150° C. under atmospheric pressure in a conventional cracking apparatus. The depolymerized cyclopentadiene should be employed or hydrogenated without substantial delay because it will redimerize on long standing at ambient temperature.

SUMMARY OF THE INVENTION

According to the invention, cyclopentadiene is selectively hydrogenated to cyclopentene in the liquid phase by passing a mixture of cyclopentadiene and hydrogen continuously through a fixed bed catalyst comprising a highly dispersed form of nickel which has been treated or saturated with ammonia or ammonium hydroxide.

The active nickel sites of the catalyst may combine with ammonia in a variety of ways. Simple divalent complexes such as $[Ni(NH_3)_2]$ can form when nickel reacts with ammonia as stated in "International Conference on Coordination Chemistry", by the Chemical Society, 1959, published by The Chemical Society, Burlington House, London.

In the presence of aqueous ammonia, nickel is capable of coordinating 6 $NH_3$ ligands in its coordination sphere as stated by J. Lewis and R. G. Wilkins in "Modern Coordination Chemistry", 1960, published by Interscience Publishers, Inc., New York, and by M. Cais in "Progress in Coordination Chemistry", 1968, published by Elsevier Publishing, New York, to give $[Ni(NH_3)_6]^{+2}$, or $[Ni(NH_3)_n(H_2O)_m]$ when insufficient ammonia is present to saturate the nickel coordination sites, where n = 1 to 6 and m = 6−n.

However, F. Basolo and R. C. Johnson state in "Coordination Chemistry", 1964, published by W. A. Benjamin, that nickel in the presence of water or hydrated nickel will form a coordination compound of the type $[Ni(OH_2)_6]^{+2}$ which will readily react with $NH_3$ to give a nickel compound with ammonia having displaced the water:

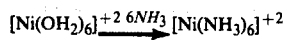

$$[Ni(OH_2)_6]^{+2} \xrightarrow{6NH_3} [Ni(NH_3)_6]^{+2}$$

DETAILED DESCRIPTION OF THE INVENTION

The temperature employed in accordance with the present invention may range from about 25° C. to about 70° C. A more preferred range is from about 40° C. to about 50° C. Temperatures that approach 100° C. tend to consume the cyclopentadiene in side reactions and, therefore, generally are not desirable. General speaking, both the temperature and the pressure of the hydrogen employed should be kept as low as possible consistent with reasonable rates of hydrogenation. When faster rates of hydrogenation than that being obtained is desired, it is preferable to increase the hydrogen pressure rather than an increase in the temperature. The most desired temperature will depend upon the flow rate, the pressure and the catalyst activity that are used to carry out the reaction. However, it has been observed that temperatures much above 70° C. tend to oligomerize the cyclopentadiene and also tend to convert the product cyclopentene to cyclopentane.

The reaction pressure employed in the present invention is generated by the addition of hydrogen. The hydrogen pressure may range from about atmospheric to 13780 to 27560 kPa — 2000 to 4000 psig; however, hydrogen pressures of 344.5 to 1033.5 kPa — 50 to 150 psig is preferred, with a hydrogen pressure of about 689 kPa — 100 psig being most preferred.

The residence time is usually defined in terms of liquid hourly space velocity (LHSV). LHSV is defined as the volume of liquid cyclopentadiene passed over or through the catalyst in one hour divided by the volume of the total catalyst. In the practice of the present invention, the LHSV chosen, of course, depends on the reaction temperature, the hydrogen pressure and the catalyst activity. However, the LHSV may be employed in a rather broad range. It has been observed that good results are obtained when the LHSV ranges from 0.5 to 15.0 with a more preferred range of from 1.0 to 10.0 and a most preferred range of from 1.5 to 5.0.

The catalyst employed in the present invention is a highly dispersed form of nickel. However, a Raney nickel-type catalyst is preferred. Methods for preparing the Raney nickel catalyst which are useful in this invention are known and can be found in a book entitled "CATALYTIC HYDROGENATION", by Robert L. Augstine, published in 1965 by Marcel Dekker, Inc., New York, N.Y.

Temperatures employed to prepare Raney nickel do not vary widely and are disclosed in this reference. The author refers to these Raney nickel catalysts as W1, W2, W3, W4, W5, W6, W7 and W8. In addition to the W-type Raney nickel, a Raney nickel referred to as T-1 is preferred, or a modification of T-1 Raney nickel is preferred.

In the Journal of Organic Chemistry 26, 1625 (1961), there is described a process for the preparation of what the authors refer to as T-1 Raney nickel by Dominguez, Lopez and Franco. In this article, the authors state that the preparation of the T-1 Raney nickel catalyst is a modification of the procedure described by Papa, Schwenk and Whitman in the Journal of Organic Chemistry 7, 586, (1942) and Papa, Schwenk and Brieger in the Journal of Organic Chemistry, 14, 366, (1949). All of the Raney nickels described in the articles referred to above are operable in the process of this invention.

Other nickel catalysts useful in the invention can be obtained by the use of new techniques known to the catalyst art for depositing metals on suitable supports in a highly dispersed form. These nickel catalysts would exhibit catalytic properties similar to the properties exhibited by the Raney nickel catalysts.

In the article by Dominguez et al, the authors state that the T-1 Raney nickel is prepared as follows:

To a one-liter 3-neck flask containing 600 milliliters (ml) of a 10 percent sodium hydroxide solution, 40 grams of Raney nickel aluminum alloy (50 percent nickel) were added in small portions over a period of 20 to 30 minutes with mechanical stirring. The temperature was kept at 90°–95° C. during this addition. The mixture was stirred for an additional hour period at which time the stirring was stopped and the nickel was allowed to settle, and the solution decanted. The metal was washed five times with 200-ml portions of water and then five times with 50-ml portions of ethanol in such a manner that the nickel was always covered with liquid. The catalyst was then stored under ethanol and refrigerated for further use.

The Raney nickel employed in some of the examples of this invention and termed by the present inventor as Modified T-1 Raney nickel was prepared by a slight modification of Dominguez et al's procedure and is as follows:

A solution of two grams of sodium hydroxide in 50 ml of water was heated to its boiling point and then there was added two grams of a granular form of Raney nickel aluminum alloy (one gram of Raney nickel) as rapidly as the hydrogen evolution would permit. This mixture was then digested at 95° to 100° C. for ¼ hour (reflux) and the water was continually replaced as it evaporated. The solution was decanted from the Raney nickel and the metal washed with three 250-ml portions of cold water. This catalyst was employed without washing with ethanol.

Whichever type of highly dispersed nickel is employed, the nickel must be treated or saturated with ammonia. The ammonia treatment of the highly dispersed form of nickel may be accomplished by directly contacting the wet nickel with gaseous ammonia. However, it is usually more convenient to employ commercially available ammonium hydroxide containing 30 percent by weight of ammonia to saturate the nickel and thereby forming the catalyst employed in the process of this invention.

It has been observed that a catalyst comprising a highly dispersed form of nickel saturated with ammonium is quite active in the hydrogenation of cyclopentadiene to cyclopentene. After continued use, the ammonia is possibly attrited from the highly dispersed nickel. In that even, one can reactivate the nickel by continuing or discontinuing the cyclopentadiene flow and resaturate the nickel with ammonia gas or ammonium hydroxide. It is quite often beneficial to periodically add a small amount of ammonia to the cyclopentadiene stream in order to reactivate the catalyst or it may be advantageous to allow a small amount of ammonia either as a gas or as ammonium hydroxide to continually flow through the catalyst to maintain its activity.

The practice of this invention is further illustrated by reference to the following examples which are intended to be representative rather than restrictive of the scope of the invention. Unless otherwise indicated, all parts and percentages are by weight.

EXAMPLE 1

A stainless steel tubular reactor of about 60 cubic centimeters volume was charged with 45 cc of granular (6 to 8 mesh U.S. Standard) of modified T-1 Raney nickel catalyst which had been saturated by soaking it with a 30 percent commercial ammonium hydroxide. The reactor was charged with hydrogen in a down flow direction and a slow stream of hydrogen was allowed to exit from the reactor through a control change at a rate of about 6 milliliters (ml) of hydrogen gas per minute. The hydrogen pressure was maintained at 100 psig — 689 kPa in the reactor. The cyclopentadiene was then brought on steam in a down flow trickle bed manner. The flow of cyclopentadiene was maintained at an LHSV of 1.87. The exothermic nature of the hydrogenation reaction raised the reactor temperature to 45° C. which was maintained with external cooling of the reactor. The cyclopentadiene bed contained a low amount of pentane which served as the gas chromatographic internal standard. The pentane contained in the cyclopentadiene was 10 grams of pentane for every 85 grams of cyclopentadiene. After the reaction had reached a steady state, about one hour, a sample was taken for gas chromatographic analysis. This analysis showed a 98 percent conversion of cyclopentadiene and a 97.2 percent selectivity to cyclopentene.

EXAMPLE 2

An experiment was conducted under the same conditions of Example 1 except that the LHSV of the cyclopentadiene was 2.52. The following results were obtained:
  94.7% conversion of cyclopentadiene
  97.6% selectivity to cyclopentene

EXAMPLE 3

An experiment was carried out under the conditions of Example 1 except that the LHSV of the cyclopentadiene was 1.25. The following results were obtained:
  99.7% conversion of cyclopentadiene
  91.0% selectivity to cyclopentene
  9.1% selectivity to cyclopentane.

EXAMPLE 4

This example is a comparative example and does not represent the practice of this invention.

An experiment was carried out under the conditions of Example 1 except that dispersed nickel was not saturated with ammonium hydroxide. The following results are obtained:
  52.8% conversion of cyclopentadiene
  90.0% selectivity to cyclopentene While certain representative embodiments and details have been shown for the purpose of illustrating the invention, it will be apparent to those skilled in this art that various changes and modifications may be made therein without departing from the spirit or scope of the invention.

What is claimed is:

1. A process for the preparation of cyclopentene which comprises selectively hydrogenating cyclopentadiene in a liquid phase by continuously passing a mixture of cyclopentadiene and hydrogen through a fixed bed catalyst comprising a highly dispersed form of nickel selected from the group comprising Raney nickel or modified Raney nickel which has been treated or saturated with ammonia or ammonium hydroxide.

2. A method according to claim 1 in which the hydrogen pressure ranges from 344.5 to 1033.5 kPa — 50 to 150 psig and the temperature ranges from about 25° C. to about 70° C. and the LHSV ranges from about 0.5 to about 15.